United States Patent
Turovskiy et al.

(10) Patent No.: US 6,666,846 B1
(45) Date of Patent: Dec. 23, 2003

(54) MEDICAL DEVICE INTRODUCER AND OBTURATOR AND METHODS OF USE

(75) Inventors: Roman Turovskiy, San Francisco, CA (US); Richard O. Murphy, Sunnyvale, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/439,646

(22) Filed: Nov. 12, 1999

(51) Int. Cl.[7] ............................................... A61M 5/178
(52) U.S. Cl. ............................. 604/164.01; 604/164.04; 128/898; 600/114
(58) Field of Search ........................... 606/1, 153, 163, 606/170, 171, 184, 185; 604/164, 165, 264, 158, 164.01, 164.04, 164.06, 164.11, 165.01, 165.02, 166.01

(56) References Cited

U.S. PATENT DOCUMENTS

| | | | | |
|---|---|---|---|---|
| 5,135,502 A | * | 8/1992 | Koenig et al. | 604/110 |
| 5,275,583 A | * | 1/1994 | Crainich | 606/184 |
| 5,380,290 A | * | 1/1995 | Makower et al. | 604/160 |
| 5,467,762 A | * | 11/1995 | Sauer et al. | 606/184 |
| 5,591,190 A | | 1/1997 | Yoon | |
| 5,607,405 A | | 3/1997 | Decker et al. | |
| 5,823,956 A | * | 10/1998 | Roth et al. | 600/374 |
| 5,843,115 A | | 12/1998 | Morejon | |
| 5,893,865 A | * | 4/1999 | Swindle et al. | 606/185 |
| 5,902,231 A | * | 5/1999 | Foley et al. | 600/102 |
| 5,904,699 A | * | 5/1999 | Schwemberger et al. | 606/185 |
| 5,928,198 A | * | 7/1999 | Lester | 128/200.26 |
| 5,931,848 A | | 8/1999 | Saadat | 606/167 |
| 5,935,103 A | | 8/1999 | Hill | 604/96 |
| 5,951,576 A | | 9/1999 | Wakabayashi | |
| 6,210,365 B1 | * | 4/2001 | Afzal | 600/435 |

* cited by examiner

Primary Examiner—Linda C. M. Dvorak
Assistant Examiner—Jocelyn Ram

(57) ABSTRACT

An introducer having an elongate tubular member and a device connector releasably attached to a proximal end of the tubular member. The introducer allows exchange of medical instruments, such as a blood filter and cardioplegia catheter, through a single lumen. An obturator having a retractable blade for making incision on a tissue is insertable through the lumen of the introducer. Methods of using the obturator and the introducer for introducing medical device (s) into body cavity, such as a vessel or cardiac tissue, are also disclosed.

7 Claims, 21 Drawing Sheets

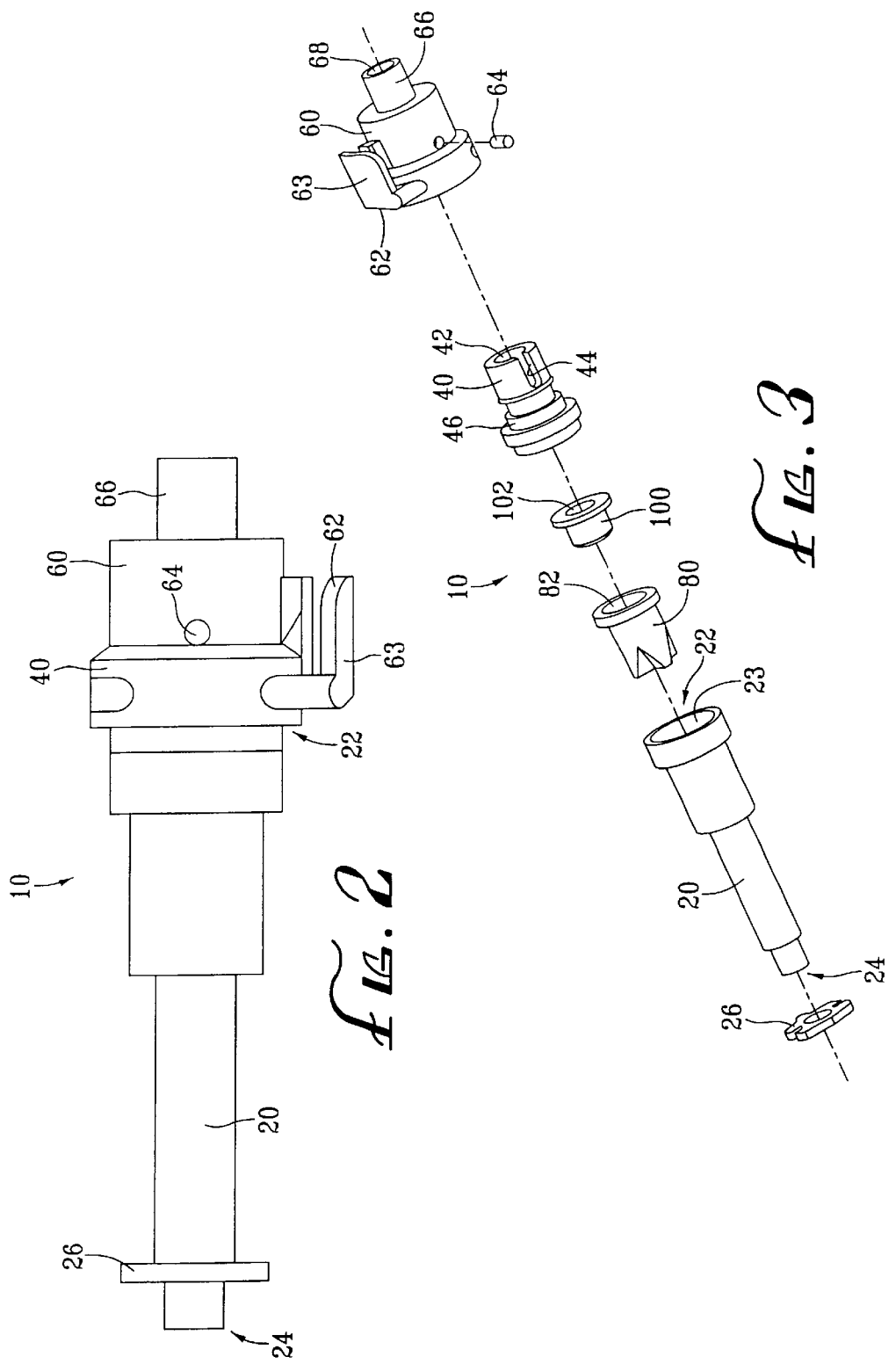

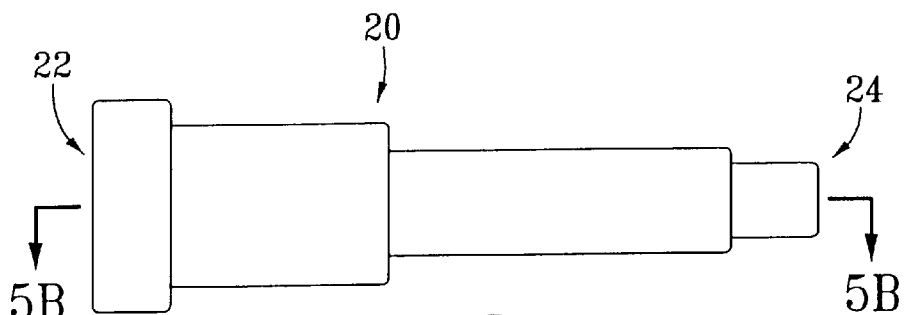
fig.5A
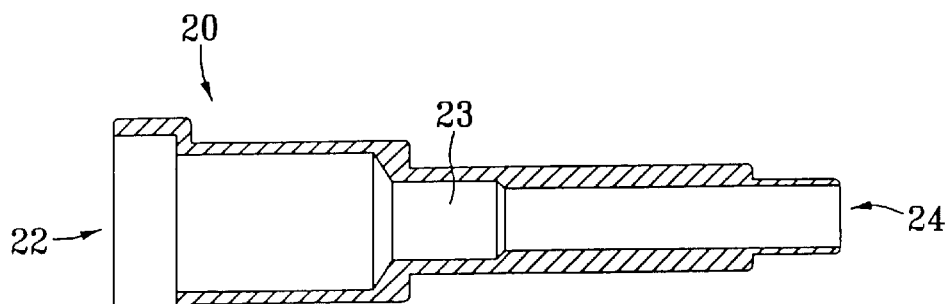
fig.5B
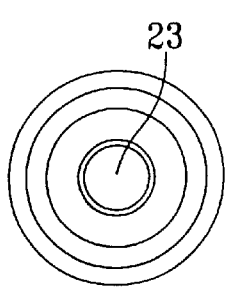 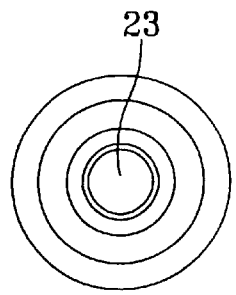
fig.5C    fig.5D

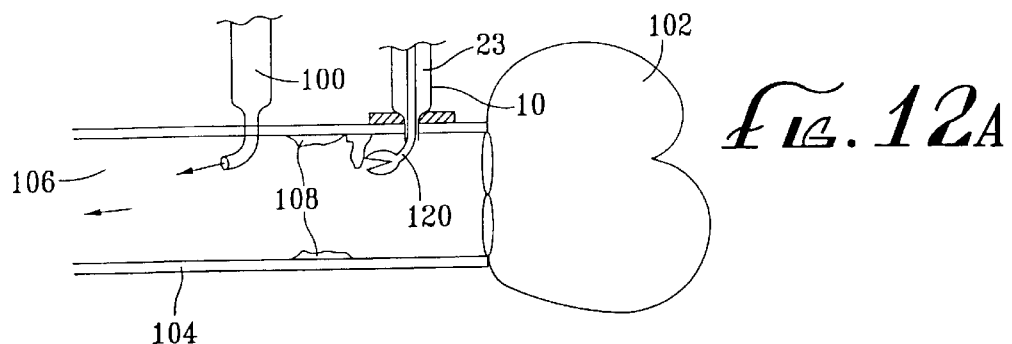
*fig.12A*
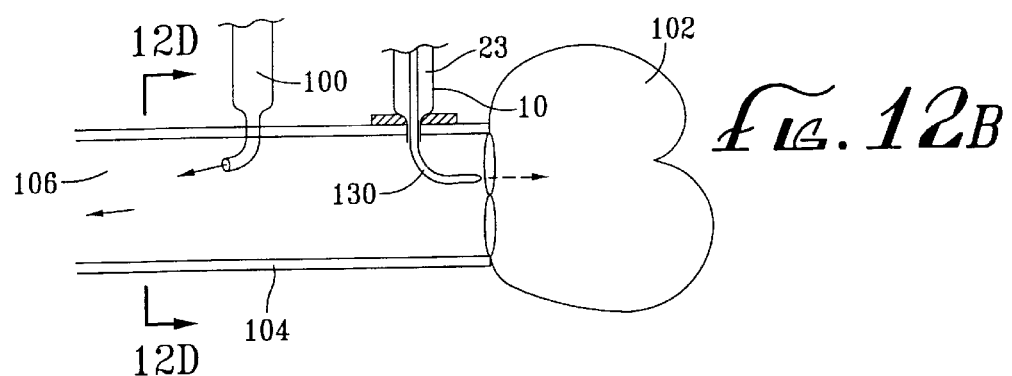
*fig.12B*
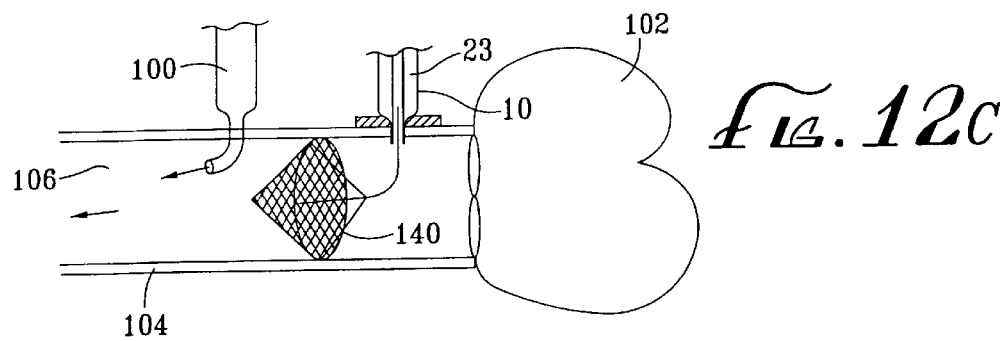
*fig.12C*
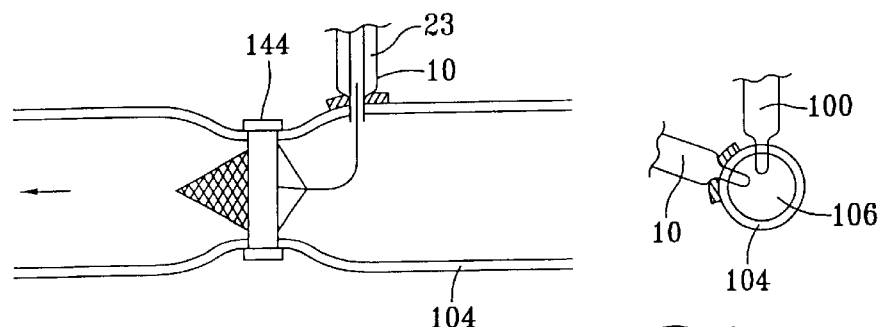
*fig.12D*        *fig.12E*

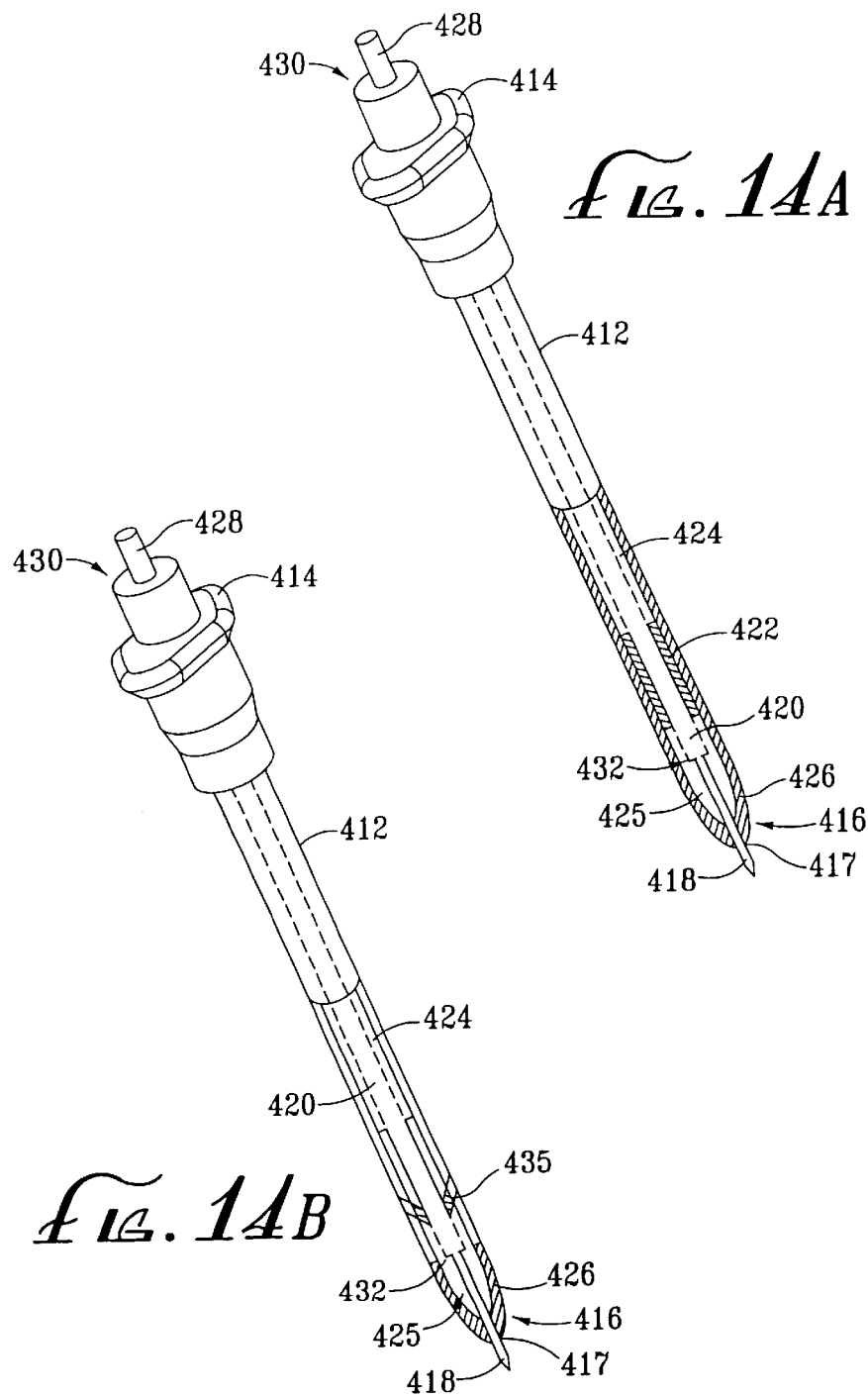

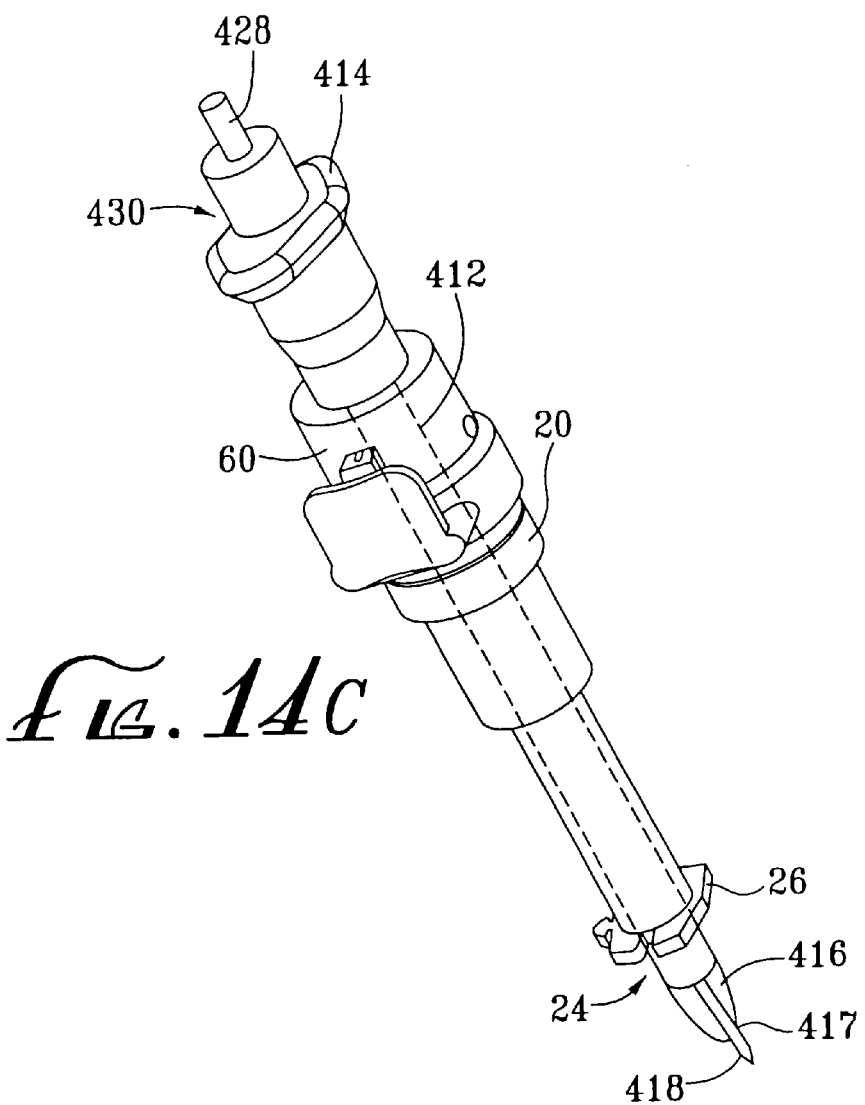

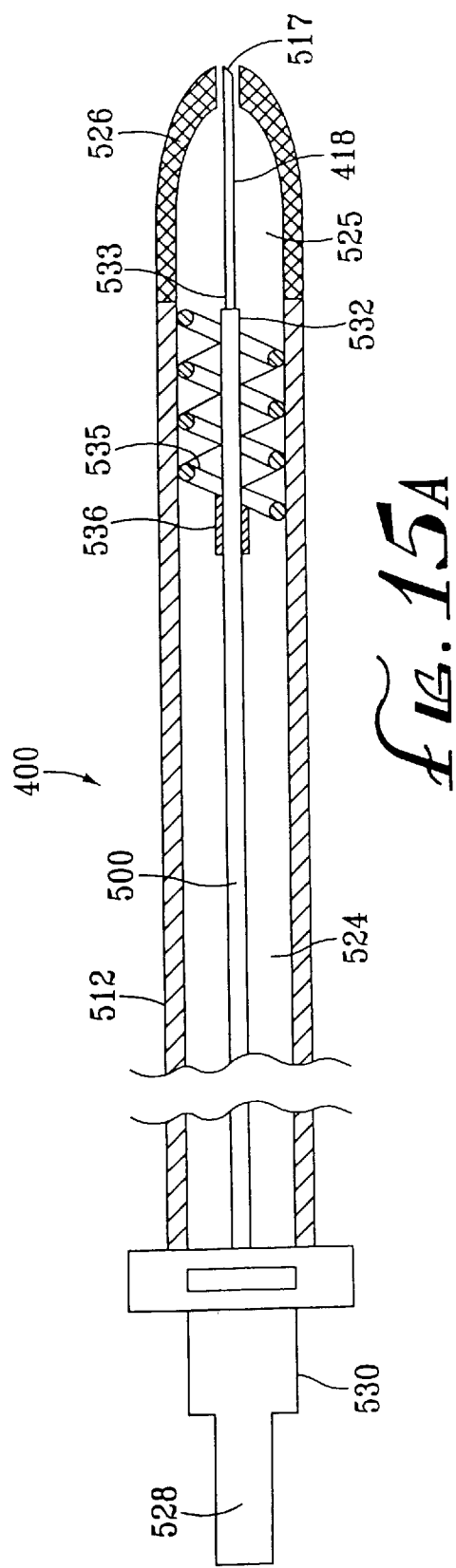

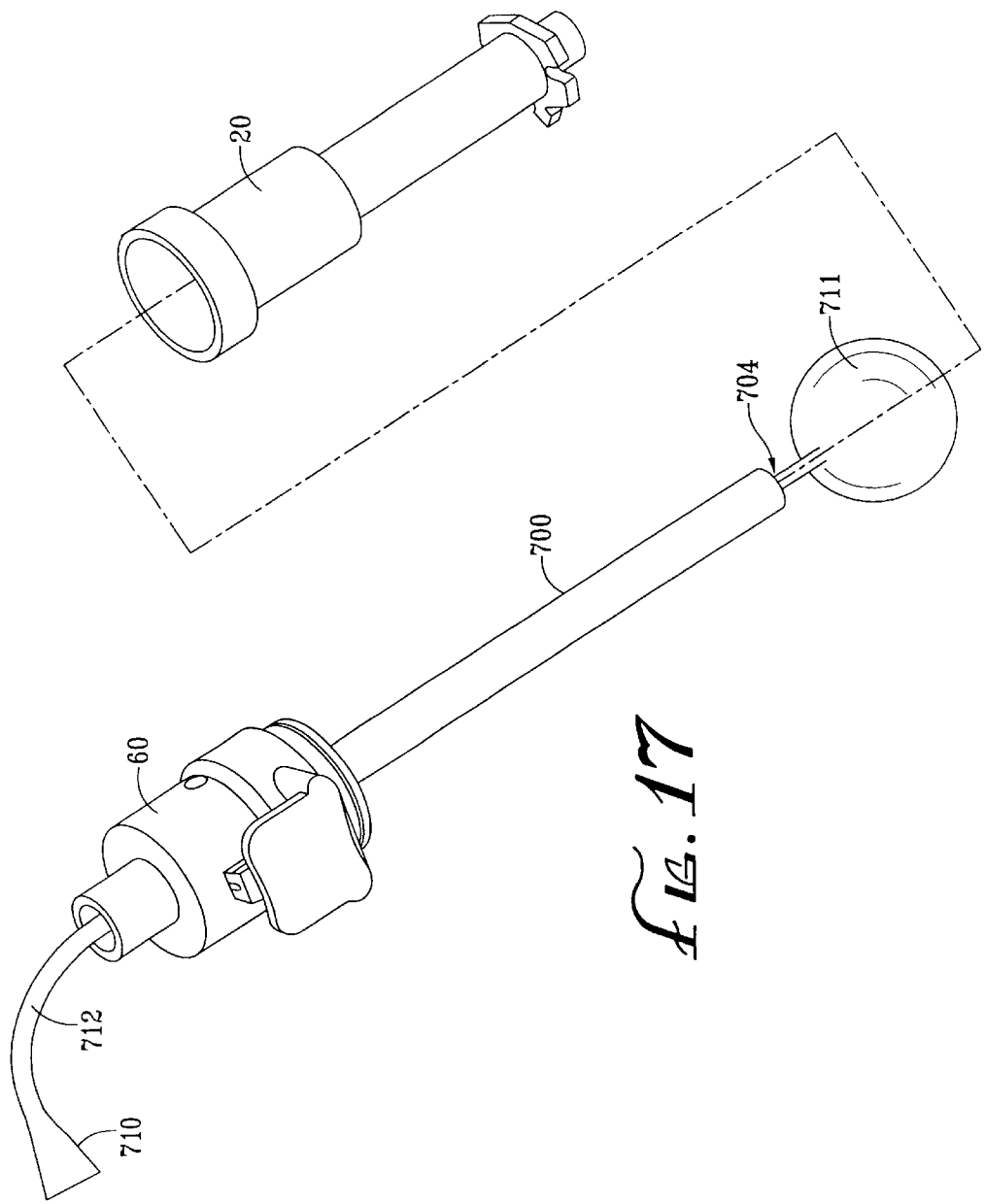

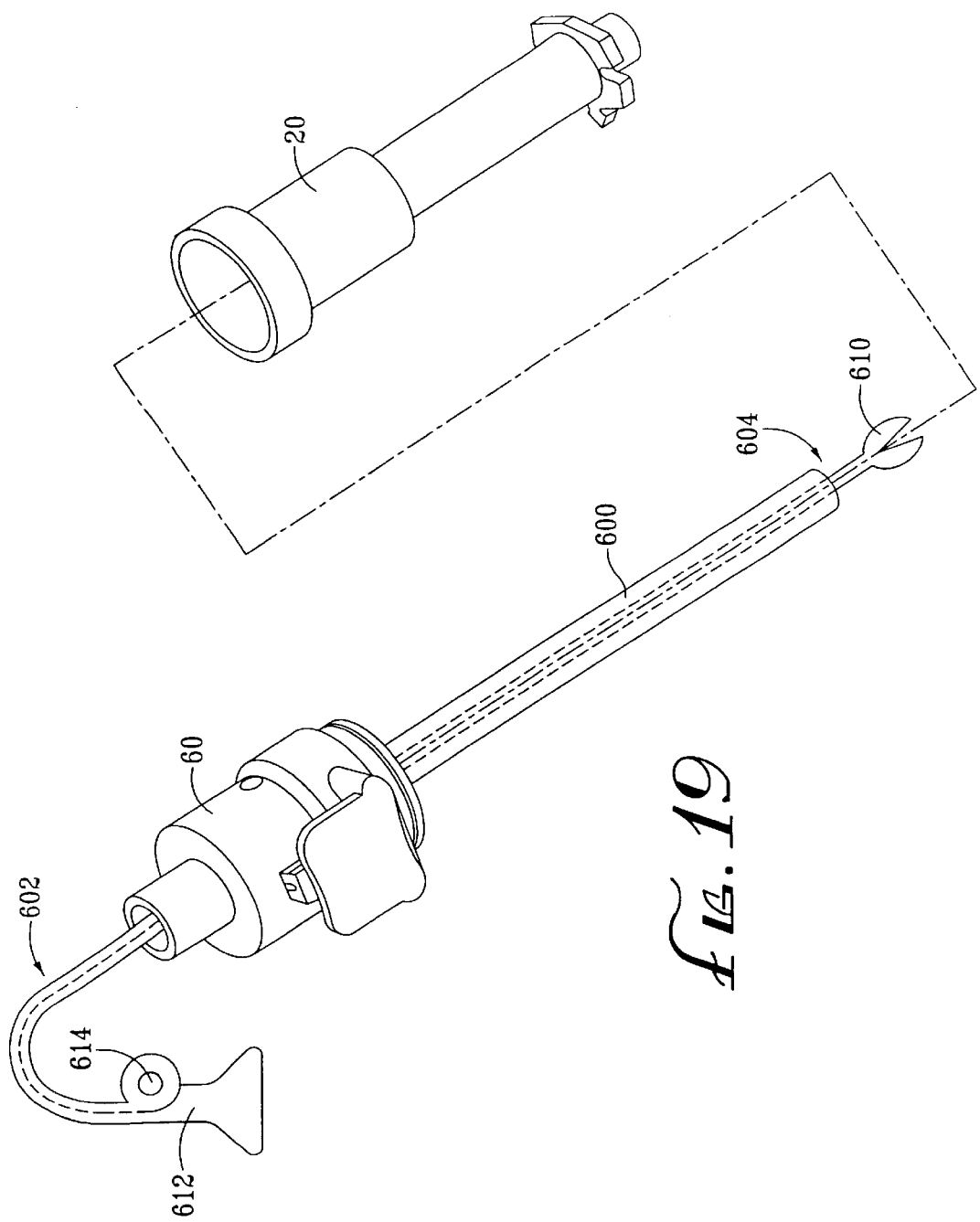

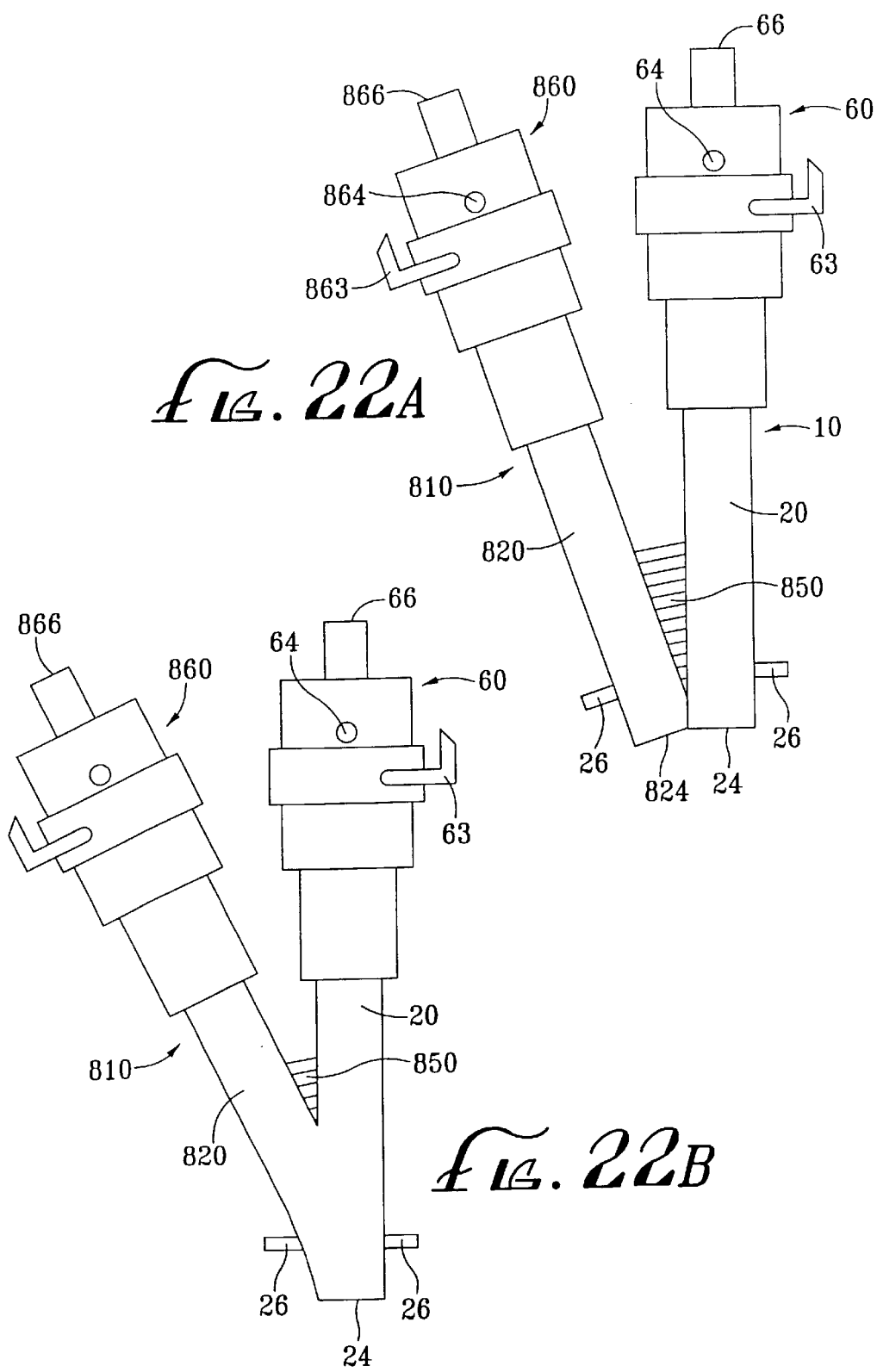

MEDICAL DEVICE INTRODUCER AND OBTURATOR AND METHODS OF USE

FIELD OF THE INVENTION

The present invention generally relates to medical devices for introducing therapeutic or diagnostic instruments, such as a blood filter, occluder, atherectomy device, stents, angiographic catheters, and pressure monitors to a vessel or cardiac tissue. More particularly, the devices include an obturator having a retractable blade for making an incision on a tissue, thereby allowing convenient and efficient delivery of medical instrument(s) through a single incision on the vessel or cardiac tissue.

BACKGROUND OF THE INVENTION

During various cardiothoracic, pulmonary, and vascular surgeries, including coronary artery bypass grafting, heart valve repair or replacement, atrial or ventricular septal defect repair, angioplasty, atherectomy, aneurysm repair, and pulmonary thrombectomy, cannulation of a patient's vessel (s) are often required to provide vascular access for delivery of various diagnostic and therapeutic devices. In a conventional approach, incisions generally made by a surgical blade are needed for introduction of medical device(s). For example, during coronary artery bypass grafting (CABG) surgeries, cardiopulmonary bypass is established by cannulation of the aorta to provide circulatory isolation of the heart and coronary blood vessels. Two incisions on the aorta may be required, i.e., one for insertion of the arterial cannula and another for insertion of a balloon occluder to provide coronary isolation from the peripheral vascular system. Once the incisions are made on the aorta, the devices often remain in the aorta throughout the entire procedure despite only being used intermittently, e.g., the cardioplegia catheter.

Due to significant mortality and morbidity associated with the conventional CABG surgeries from the use of cardiopulmonary bypass for circulatory support and the traditional method of access by median sternotomy, minimally invasive concepts recently have been adopted to make cardiothoracic procedures less invasive. Minimally invasive alternatives include the minimally invasive direct CABG procedure in which the operation is performed through minimal access incisions, eliminating cardiopulmonary bypass. The second alternative is to perform the procedure through minimal access incisions, and cardiopulmonary support is instituted through an extra thoracic approach, i.e., the port access approach. The third alternative is to perform the procedure on a beating heart which allows greater access for more extensive revascularization, i.e., the "off pump" sternotomy approach. In any of the minimally invasive alternatives, the space allowed for multiple incisions and device insertion is limited.

The disadvantages associated with the conventional or minimally invasive approach are that (1) by having multiple devices inserted in the aorta, the space available for the surgeon to perform procedures is limited, and (2) the aorta is traumatized as a result of multiple incisions, which may result in aortic dissection, aortic wall hematoma, and/or embolization of calcium plaque from the aortic wall. The greater the aortic trauma, the higher the perioperative morbidity a patient will endure.

Accordingly, there is a need for devices and methods which provide access to a vessel or body cavity and allow introduction of medical instrument(s) through a single incision, and particularly through a single introducer by exchanging medical instruments with minimal blood loss. A further need exists for devices and methods to assist with making an incision in a body cavity for the purpose of introducing an introducer while minimizing blood loss, and with maximum convenience for the physician.

SUMMARY OF THE INVENTION

The present invention provides introducers for introducing medical devices into a body tissue, such as a vessel, or cardiac tissue, for performing multiple functions including perfusion, drug deliver, fluid infusion, atherectomy, fluid pumping, aspiration, suturing, stapling, collagen or fibrin delivery, delivery of pacing leads, angiographic catheters, valvuloplasty catheters, and electrode catheters, internal vessel segregating or isolating dams, endoscopic cameras, pressure monitors, shunts, stents, graft delivery, and other endovascular and endoscopic devices. Obturators are also provided for creating an incision in body tissue. Although the introducers and obturators disclosed herein are most useful in cardiovascular procedures, they can also be used in introducing medical devices into other body cavities, e.g., gastrostomy tube placement, and abdominal or pelvic laporoscopy.

In a first embodiment, the introducer comprises an elongate tubular member and a device connector releasably attached to a proximal end of the tubular member. The objective here is to allow for the exchange of endovascular devices through a single tubular introducer. A distal end of the tubular member is adapted to enter a body tissue. The proximal end of the tubular member has, in certain embodiments, a longitudinal alignment slot extending distally from the proximal end. The device connector has a lumen communicating with a first end and a second end. The lumen is adapted to receive a medical device. A medical device is inserted and secured in the lumen of the device connector before it is inserted through the lumen of the tubular member. The connector also includes an alignment pin adapted to engage the alignment slot of the tubular member, and is shaped to engage the proximal end of the tubular member by operating a release lever.

In another embodiment, the introducer includes a second tubular member mounted adjacent to the first tubular member. The second tubular member has a proximal end with a proximal port, a distal end with a distal port and a lumen communicating between the proximal and distal ports. The second tubular member also includes a second connector having a lumen adapted to reversibly engage the proximal end of the second tubular member, and to receive a second medical device through the second connector lumen. The second medical device is inserted through the second tubular member and is deployable through the distal port of the second tubular member. In certain embodiments, the distal port of the first tubular member communicates with the distal port of the second tubular member, such that the first and second medical devices are deployed through a common distal port. In other cases, the lumens remain separate and communicate with separate distal ports.

The lumens of the tubular member and the device connector are also adapted to receive an obturator for making an incision on a body tissue. In a first embodiment, the obturator comprises an elongate tubular member having proximal and distal ends. The distal end has a slot which extends proximally, and includes a blade which connects to a distal end of an actuating mechanism. The actuating mechanism generally includes a force-biasing element, such as a spring, a retaining element, and a release. The blade can be advanced distally to incise a tissue, or retracted to a position within the slot by operating the actuating mechanism from the proximal end of the elongate tubular member. The obturator is insertable through the lumen of the introducer or can be used independently to incise a body tissue, e.g., a vessel, cardiac tissue, gallbladder, or stomach.

In a first method of using the obturators and introducers described above for introduction of a medical device, the obturator, having the blade in a retracted position, is inserted through the lumen of the introducer to create an incision on a body tissue. The blade extends distally beyond the distal end of the obturator by operating the actuating mechanism at the proximal end of the obturator, such that the actuating mechanism slides distally against the force-biasing element and is retained in a distal position. After an incision is made in the body using the blade, the introducer is inserted though the incision. The actuating mechanism is then released and slides proximally to retract the blade into a position within the slot, and the obturator is removed from the introducer. A hemostatic valve mounted within the lumen of the introducer prevents blood loss. A medical device is inserted through the lumens of the device connector and secured, and the device is then inserted into the tubular member of the introducer. The device is then advanced into the body tissue. When present, the alignment pin is aligned with the longitudinal slot of the tubular member, and the device connector snaps into engagement with the proximal end of the tubular member. In certain embodiments, a suture flange is provided on the distal end of the introducer, and sutures can be placed on the flange to stabilize the introducer and the medical device onto the body tissue.

In another method, the incision on the body tissue is created by holding the obturator directly adjacent the body tissue and operating the actuating mechanism to advance the blade without placing the obturator in the lumen of the introducer. After the incision is made, the introducer is inserted through the incision for introducing medical devices.

Additional features of the present invention will become apparent from consideration of the following description taken in conjunction with the accompanying drawings.

BRIEF DESCRIPTION OF THE DRAWINGS

FIG. 2 depicts a lateral view of the introducer of FIG. 1.

FIG. 3 depicts an exploded view of the introducer of FIG. 1.

FIG. 5A depicts a lateral view of a tubular member of the introducer of FIG. 3.

FIG. 5B depicts a cross-sectional view of the tubular member of FIG. 5A through sectional line B—B.

FIG. 5C depicts a proximal view of the tubular member of FIG. 5A.

FIG. 5D depicts a distal view of the tubular member of FIG. 5A.

FIG. 12A depicts an atherectomy device inserted through the introducer of FIG. 3 during cardiac surgery.

FIG. 12B depicts a cardioplegia catheter inserted through the introducer of FIG. 3 during cardiac surgery.

FIG. 12C depicts a filter device inserted through the introducer of FIG. 3 during cardiac surgery.

FIG. 12D depicts placement of a cinch around the filter of FIG. 12C.

FIG. 12E depicts a cross-sectional view of the aorta of FIG. 12B through sectional line D—D.

FIG. 14A depicts an embodiment of an obturator having cutting capabilities constructed according to the present invention.

FIG. 14B depicts another embodiment of an obturator having a force-biasing element.

FIG. 14C depicts the obturator of FIG. 14A inserted into the introducer of FIG. 3.

FIG. 15A depicts another embodiment of the obturator carrying a retractable blade.

FIG. 17 depicts a balloon occluder inserted through the introducer of FIG. 3.

FIG. 19 depicts an atherectomy device inserted through the introducer of FIG. 3.

FIG. 22A depicts two introducers attached at their distal region.

FIG. 22B depicts the introducers of FIG. 22A having a common distal port.

DETAILED DESCRIPTION

Figure 1:
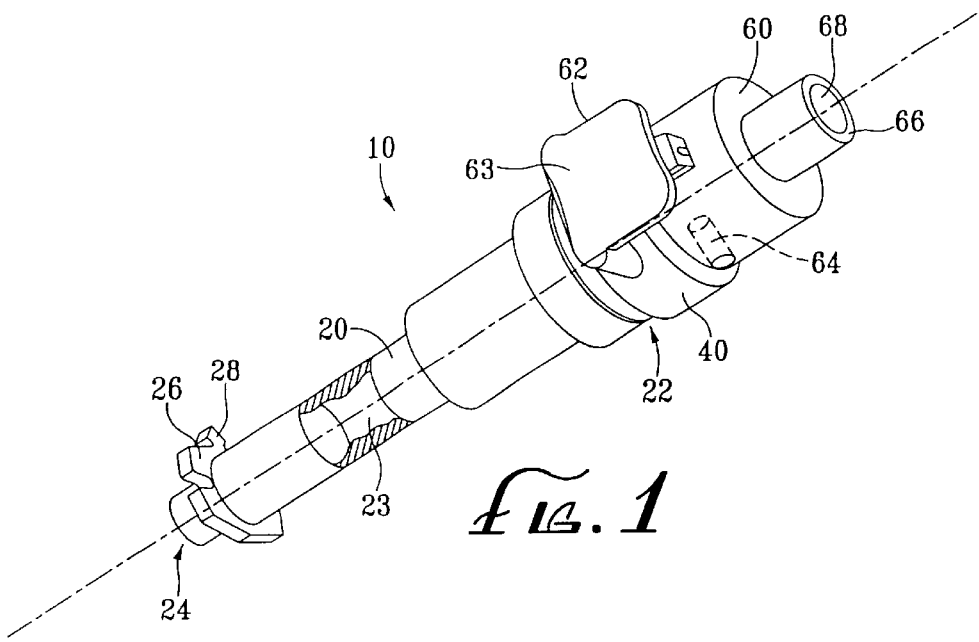
FIG. 1 depicts an embodiment of an introducer constructed in accordance with the present invention.

Referring now to the drawings, FIGS. 1–3 depict an embodiment of introducer 10 constructed in accordance with the present invention. Introducer 10 comprises elongate tubular member 20 having proximal end 22, distal end 24, and device connector 60 which reversibly engages proximal end 22. Tubular member 20 has lumen 23 which communicates with proximal end 22 and distal end 24. Suture flange 26 is mounted on distal end 24 and includes orientation marker 28 to facilitate positioning of the introducer in a body tissue when multiple medical devices are introduced.

Figure 1B:
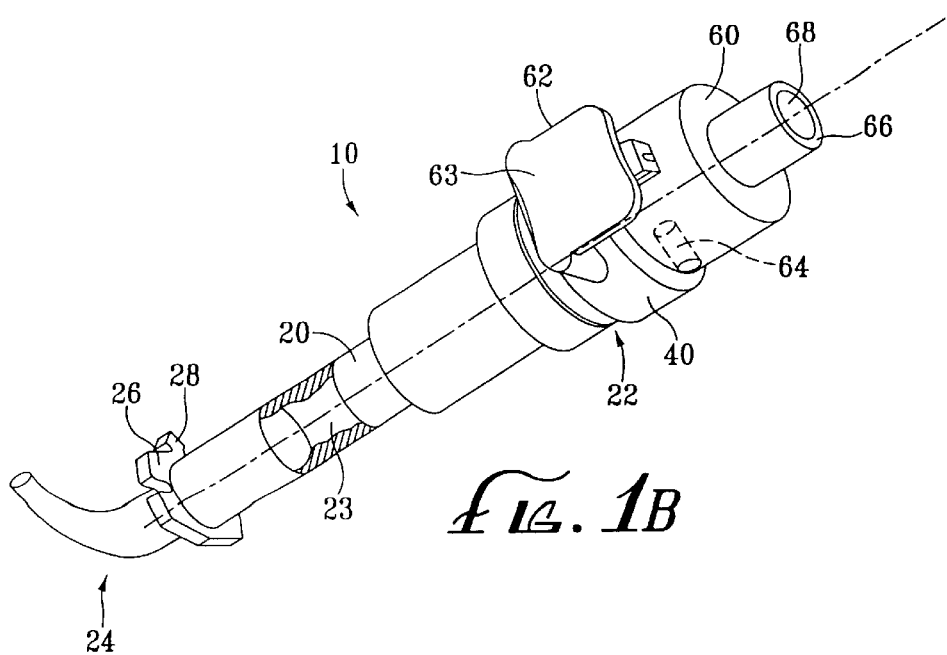
FIG. 1B depicts another embodiment of the introducer having a curved distal end.

In FIG. 1B, distal end 24 of elongate tubular member 20 is curved. This design is desirable for introduction of endovascular devices which require directional deployment in a vessel, e.g., deployment of an endoscope or atherectomy device in the aorta.

In FIG. 3, one-way valve 80 which has lumen 82, and wiper 100 which has lumen 102 are attached to proximal end 22 of tubular member 20. Lumens 82 and 102 communicate with lumen 23 of the tubular member. In certain embodiments, valve 80 is a hemostatic valve which prevents back flow of blood through the introducer during insertion into vascular tissue. Cap 40 is connected proximally to wiper 100 at proximal end 22 of the tubular member. Cap 40 includes lumen 42, alignment slot 44, and fastening member 46 disposed distal to the alignment slot. The fastening member has either a slightly raised or depressed surface or alternatively comprises another common fastener. When cap 40 is connected to tubular member 20, lumen 42 communicates with lumen 23, lumen 82, and lumen 102.

Figure 4A:
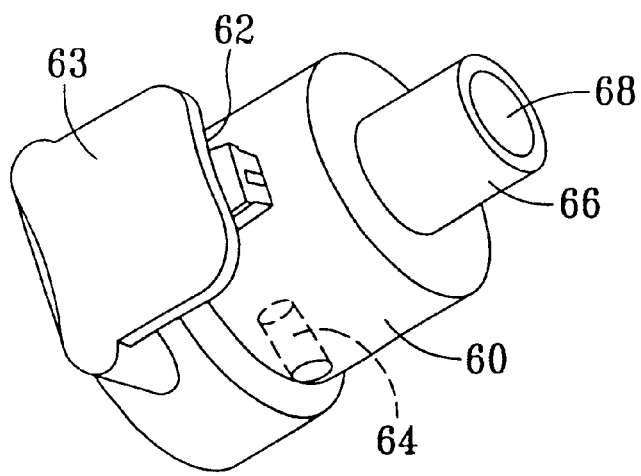
FIG. 4A depicts an embodiment of a device connector constructed in accordance with the present invention.
Figure 4B:
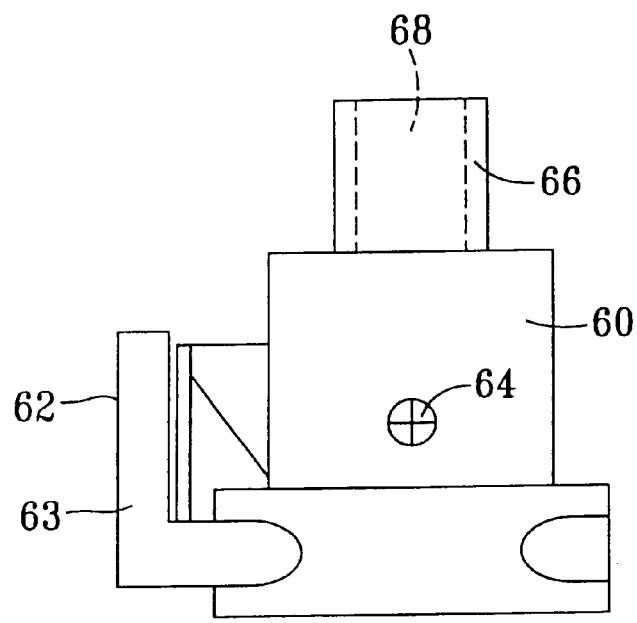
FIG. 4B depicts a lateral view of the device connector of FIG. 4A.

Device connector 60 includes releasable engaging mechanism 62 and alignment pin 64. Alignment pin 64 engages alignment slot 44 for proper attachment of device connector 60 to cap 40. In this way, device connector 60 is attached to cap 40 in a specified orientation. Engaging mechanism 62 is biased to grip fastening member 46 when device connector 60 is placed on cap 40, thereby allowing firm attachment between the device connector and the cap. Release lever 63 is attached to engaging mechanism 62. By depressing lever 63, device connector 60 is removed from cap 40 by disengaging mechanism 62. In FIGS. 4A and 4B, the device connector also includes lumen 68 at proximal end 66, which is adapted for insertion of medical devices.

In FIG. 5A, a lateral view of tubular member 20 is provided. A cross-sectional view of the tubular member showing lumen 23 adapted for insertion of medical devices from proximal end 22 to distal end 24 is shown in FIG. 5B. Proximal and distal views of tubular member 20 are shown respectively in FIGS. 5C and 5D.

Figure 6:
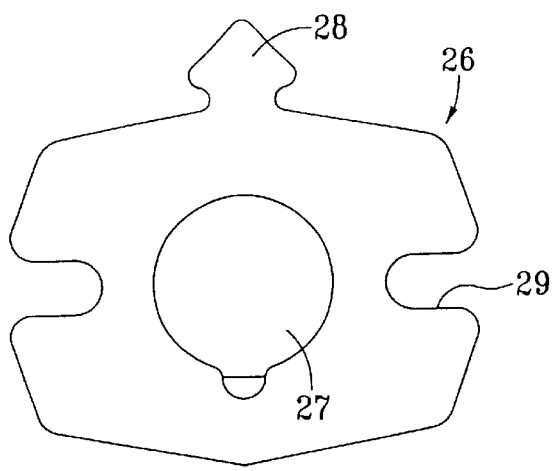
FIG. 6 depicts an embodiment of a suture flange constructed in accordance with the present invention.

The design of suture flange 26 is depicted in FIG. 6. The flange is either mounted or slideably disposed about a distal region of the tubular member through aperture 27. Flange 26 also includes orientation marker 28 which facilitates positioning of a medical device during insertion. Recessed openings 29 allow placement of sutures for securing the introducer to a body tissue.

Figure 7A:
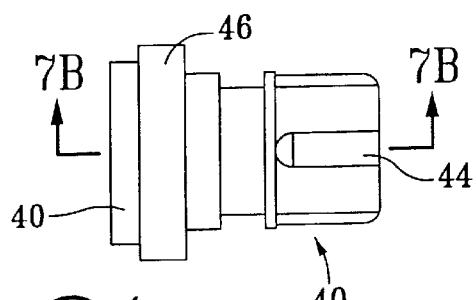
FIG. 7A depicts an embodiment of a cap mounted on a proximal end of the introducer of FIG. 3.
Figures 7B, 7C:
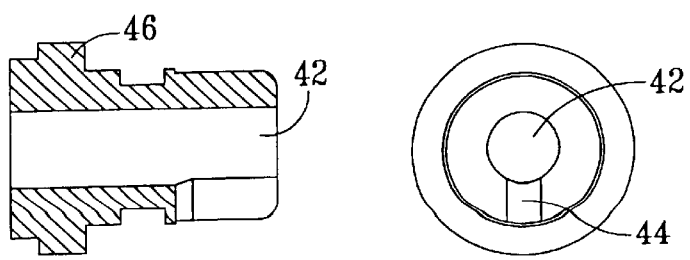
FIG. 7B depicts a cross-sectional view of the cap of FIG. 7A through sectional line B—B.
FIG. 7C depicts a proximal view of the cap of FIG. 7A.

FIG. 7A depicts a lateral view of cap 40 having alignment slot 44 and fastening member 46. FIG. 7B provides a cross-sectional view of the cap having lumen 42, adapted for insertion of a medical device. FIG. 7C provides a proximal view of the cap of FIG. 7A, which demonstrates the relationship of alignment slot 44 to lumen 42.

Figure 8A:
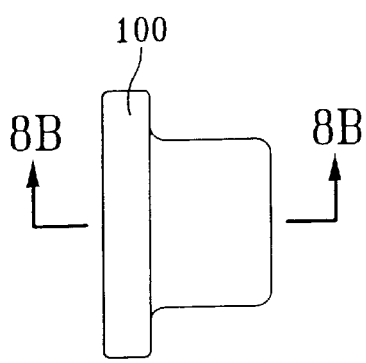
FIG. 8A depicts an embodiment of a wiper included in the introducer of FIG. 3.
Figure 8B:
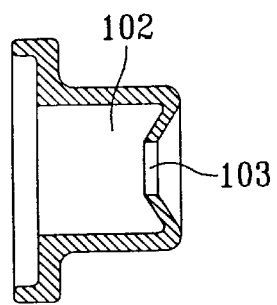
FIG. 8B depicts a cross-sectional view of the wiper of FIG. 8A through sectional line B—B.
Figure 8C:
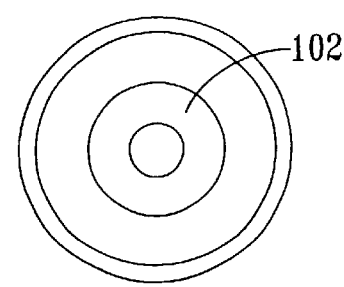
FIG. 8C depicts a distal view of the wiper of FIG. 8A.

Referring to FIGS. 8A, 8B, and 8C, wiper 100 includes partial sealing and cleaning mechanism 103 located at the center of lumen 102 which allows a device to pass unrestricted while wiping or cleaning the device. The sealing and cleaning mechanism 103 can be pre-treated with a sterilizing agent or an anti-coagulant, e.g., heparin.

Figure 9:
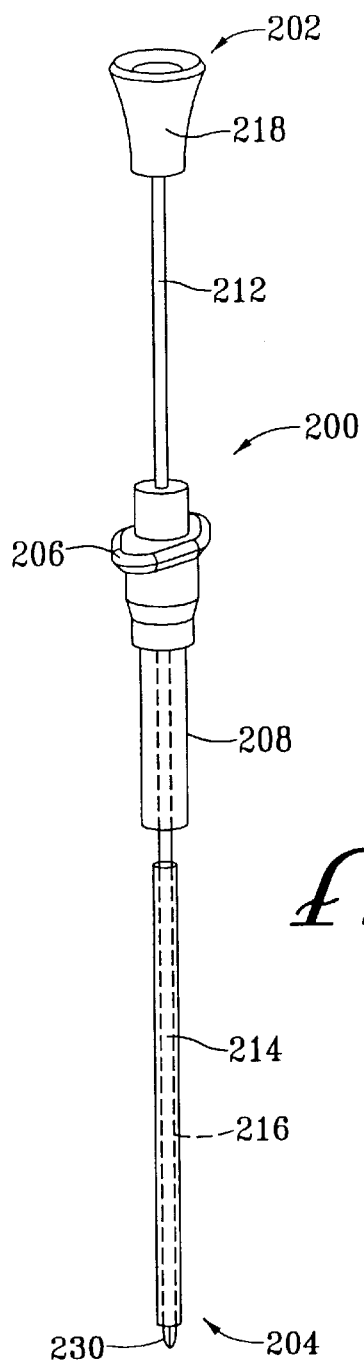
FIG. 9 depicts an embodiment of a filter device adapted for insertion into an introducer.

The introducers described above can be used for deployment a variety of medical devices into a body cavity, such as blood filter 200 depicted in FIG. 9. The filter is often used during carotid atherectomy heart valve repair, or coronary artery bypass graft surgery to capture embolic material, e.g., calcium, atheromatous plaque, tissue debris, gaseous bubbles, or thrombi generated during the surgery. The filter is described in detail in U.S. Pat. Nos. 5,846,260, 5,769,816, 5,662,671, 5,910,154, and 5,876,367, all incorporated herein by reference in their entirety. Blood filter 200 comprises tubular member 208, which includes gripping element 206 for holding the filter during operation of the filter. Second tubular member 214, having lumen 216, is housed within tubular member 208. Elongate member 212 is slideably inserted in second tubular member 214, which has proximal end 202 and distal end 204. Actuating handle 218 is mounted on proximal end 202, and expandable filter 230 is mounted on distal end 204. In certain embodiments, a porous filter is mounted on proximal end 202 to allow escape of air or gas but not blood or fluid through the proximal end. Filter 230 is retracted within the lumen 216 of the second tubular member.

Figure 10:
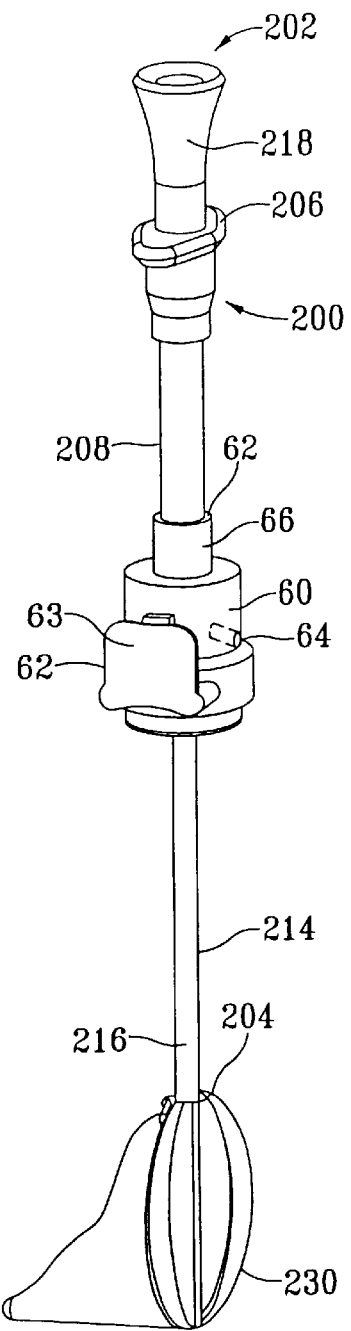
FIG. 10 depicts the filter device of FIG. 9 inserted through the device connector of FIG. 3.

In using the filter of FIG. 9 with the device connector of FIG. 3, filter 200 is inserted through the lumen of device connector 60 as shown in FIG. 10. Tubular member 208 of the filter engages proximal end 66 of the device connector via a releasable engaging mechanism such as a clip or snap or by a simple compression fitting. Filter 230 is expanded by applying force to actuation handle 218, thereby advancing elongate member 212 distally through lumen 216.

Figure 11:
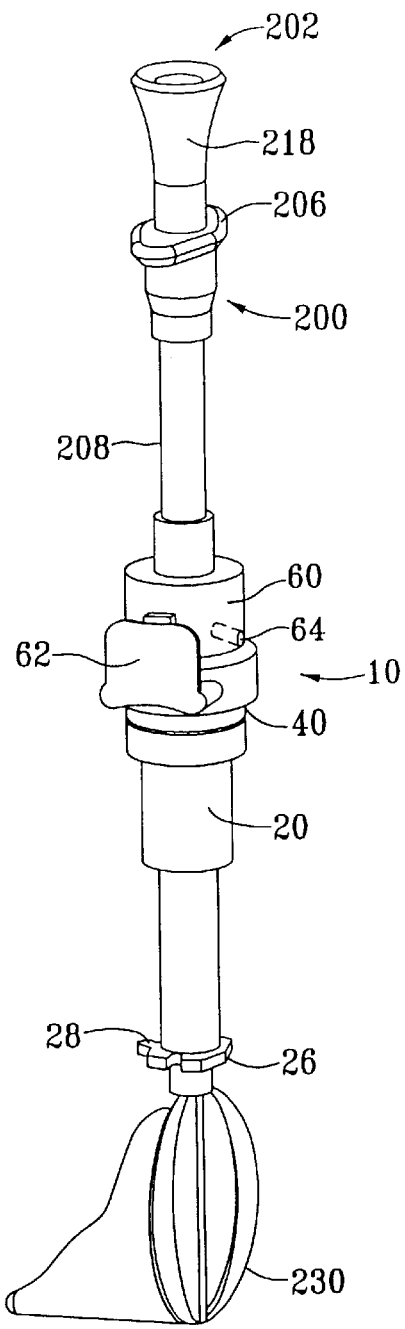
FIG. 11 depicts the filter/device connector of FIG. 10 inserted into the tubular member of FIG. 3.

After filter device 200 is secured in the device connector, the second tubular member of the filter is inserted through the lumen of tubular introducer 20 as depicted in FIG. 11. Device connector 60 attaches to tubular member 20 by having alignment pin 64 engage the alignment slot of cap 40. By depressing lever 62, device connector 60 can be removed from tubular member 20. Filter 230 is preferably placed in a retracted/collapsed state to facilitate insertion into and removal from the introducer. After the introducer is inserted into a vascular tissue, such as the aorta or the right atrium, filter 230 is deployed by advancing actuating handle 218 distally. Sutures can be placed on support flange 26 to secure the introducer onto the vascular tissue. Orientation marker 28, which is mounted on flange 26, provides proper alignment of the medical device within the blood vessel.

The introducer disclosed herein can be used to introduce a variety of medical devices. Multiple devices can be sequentially introduced into a body cavity through the same device introducer, thereby reducing the potential for trauma to the body tissue, and reducing the number of incisions. Furthermore, the medical devices can be independently introduced without compromising the location and orientation of other instruments used during the procedure. For example, referring to FIGS. 12A, 12B, and 12C, during coronary artery bypass graft (CABG) surgery, arterial cannula 100 is often inserted downstream in aorta 104 for delivering oxygenated blood from a bypass-oxygenator through lumen 106 of the aorta. In FIG. 12A, atherectomy device 120 is inserted through lumen 23 of introducer 10 to remove mobile plaque 108 on the aortic wall. To deliver cardioplegia, atherectomy device 120 is removed and a cardioplegia catheter is inserted into the introducer as shown in FIG. 12B to deliver cardioplegic solution upstream to heart 102. When insertion of a blood filter is desired to capture embolic material generated, especially during clamping or unclamping of the aorta, cardioplegia catheter 130 is removed and expandable filter 140 is deployed through the introducer, as shown in FIG. 12C. In this way, various devices can be deployed in aortic lumen 106 through one introducer without removing or inserting additional introducer(s), thereby reducing trauma to the aortic wall. In FIG. 12D, cinch strap 144 is placed around the outer aortic wall to optimize contact between filter 140 and inner aortic wall, when the diameter of the expanded filter is smaller than the aortic diameter. This technique allows the use of a single filter size to fit any size aortic lumen, as the vessel is compressed to fit the filter.

The introducers disclosed herein are particularly useful in minimally invasive procedures where surgical space is limited for multiple device insertion. It will be understood that the introducer can also be used on non-vascular tissues, e.g., the stomach during gastrostomy tube insertion, or on the bile duct during stent placement. The introducer can be inserted at the same radial position but longitudinally displaced from blood cannula 100 or at a different radial position as the blood cannula as depicted in FIG. 12E, thereby providing greater flexibility for the surgeon.

Figure 13:
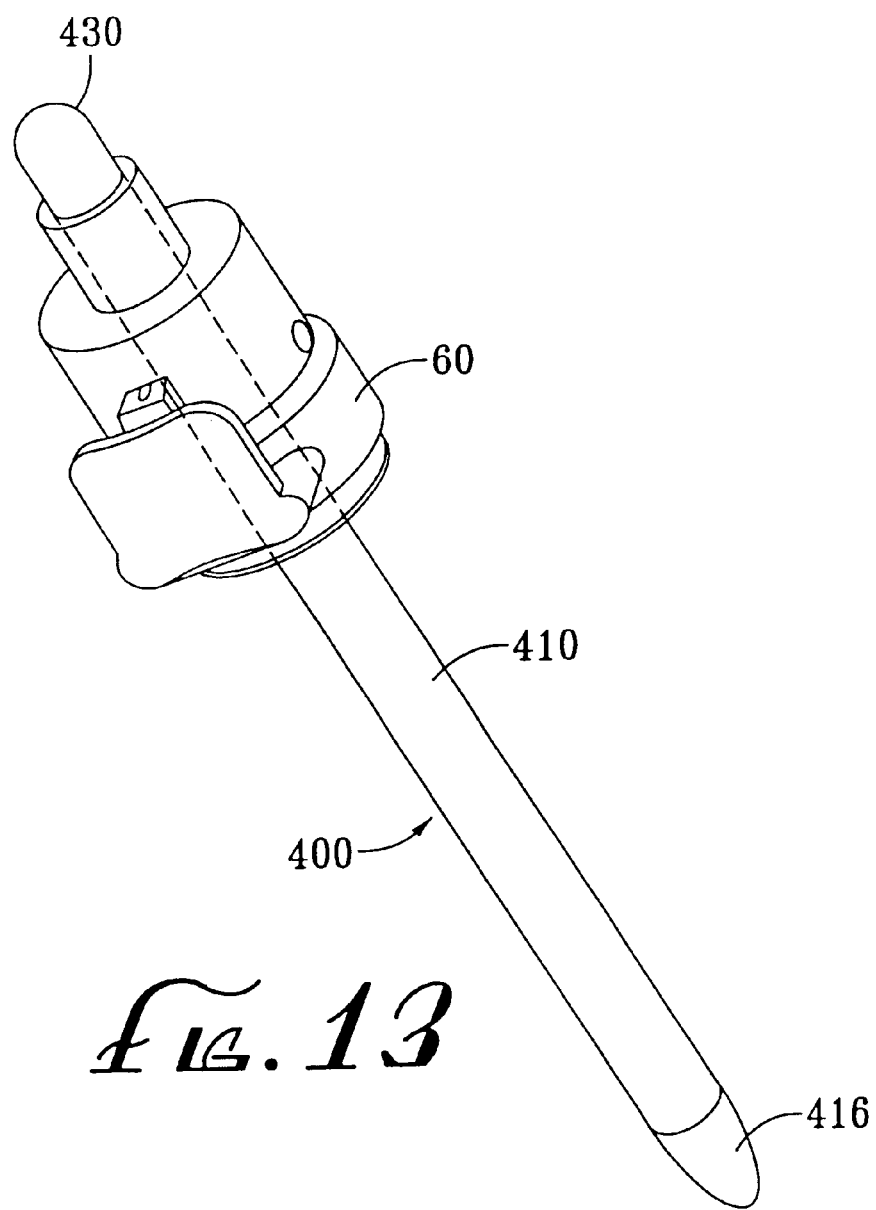
FIG. 13 depicts an obturator inserted through the device connector of FIG. 3.

An obturator is often inserted into an introducer prior to introduction of medical devices. FIG. 13 depicts device connector 60 engaging obturator 400, which comprises tubular member 410 having proximal end 430 and distal end 416. Distal end 416 is adapted to slideably insert into the lumen of the introducer.

The present invention provides an obturator having cutting capabilities for facilitating insertion of an introducer into body tissue. FIG. 14A depicts an embodiment of the obturator which comprises elongate tubular member 412 having proximal end 430 and distal end 416. Gripping element 414, which facilitate handling of the obturator, is mounted on proximal end 430. Distal end 416 has slot 425 within tubular casing 426. The obturator also includes an actuating mechanism 420 housed in lumen 424 of tubular member 412. The actuating mechanism has proximal end 428, and distal end 432 which terminates proximal to slot 425 of tubular member 412. A blade, scapal, or other suitable cutting element 418 is mounted on distal end 432, and is housed within slot 425. Casing 426 includes aperture 417 which allows cutting element 418 to extend distally. The actuating mechanism also includes deployment mechanism 422, which allows cutting element 418 to extend distally through aperture 417 when a force is applied to proximal end 428 of the actuating mechanism. The deployment mechanism maintains cutting element 418 in this extended position until a force is again applied to proximal end 428, causing the cutting element to retract within slot 425.

FIG. 14B depicts another embodiment of the obturator having a force biasing mechanism, such as spring 435. In use, a force is applied to proximal end 428 of actuating mechanism 420, causing cutting element 418 to extend through aperture 417. Spring 435 maintains a continuous proximal force on cutting element 418, so that when the actuator is released from proximal end 428, the spring automatically retracts and returns cutting element 418 to slot 425. In this way, accidental damage to tissue by the cutting element can be prevented.

In using the obturator of FIG. 14A with an introducer, the obturator is first inserted through device connector 60 and subsequently into the lumen of the introducer as shown in FIG. 14C. Distal end 416 of the obturator extends distal to distal end 24 of the introducer. The obturator/introducer assembly is then positioned adjacent a body tissue, and a force is applied to proximal end 428 of the obturator to advance cutting element 418 distally through aperture 417 to incise the body tissue. The cutting element is preferably retracted by operating the actuating mechanism prior to insertion of obturator/introducer assembly through the incision. Sutures can then be placed on flange 26 to secure the introducer onto the body tissue. The obturator and device connector are then removed from the introducer, and the obturator is then removed from the device connector. A medical device is inserted into the device connector and deployed into the body tissue after the device/connector assembly is advanced to the introducer.

FIG. 15A depicts another embodiment of an actuating mechanism for advancing blade 418. Obturator 400 comprises elongate tubular member 512 having lumen 524, which houses the actuating mechanism. The mechanism comprises elongate member 500 having proximal end 528 and distal end 532, which connects to proximal end 533 of blade 418. The blade is housed in slot 525 of casing 526, which is releasably attached to the distal end of tubular member 512. A force-biasing element, shown here as spring 535, is held in a compressed state by stop 536. The actuating mechanism is operated at proximal end 530 of the obturator to extend blade 418 through aperture 517.

Figure 15B:
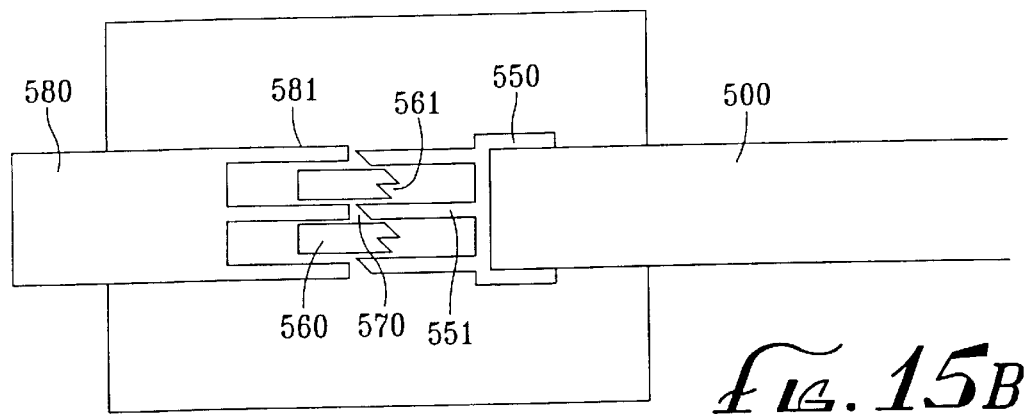
FIG. 15B depicts a proximal end of the obturator of FIG. 15A with the blade retracted within the obturator.
Figure 15C:
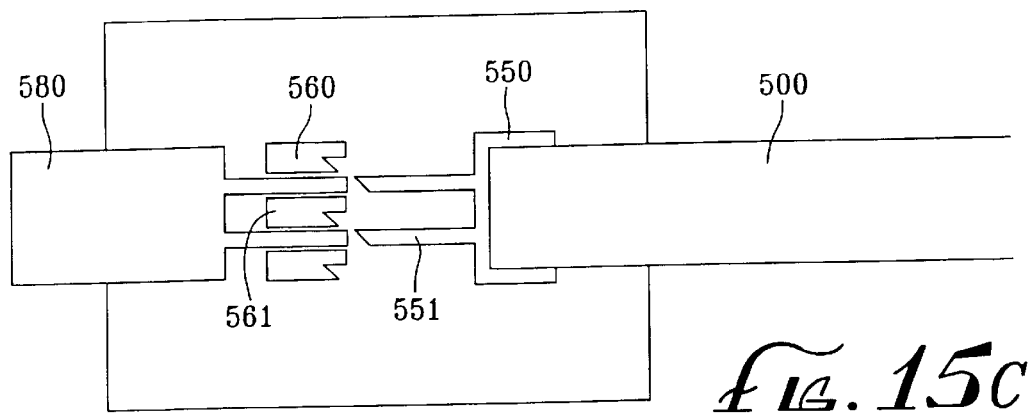
FIG. 15C depicts the proximal end of the obturator of FIG. 15B when a force is applied to a release element.
Figure 15D:
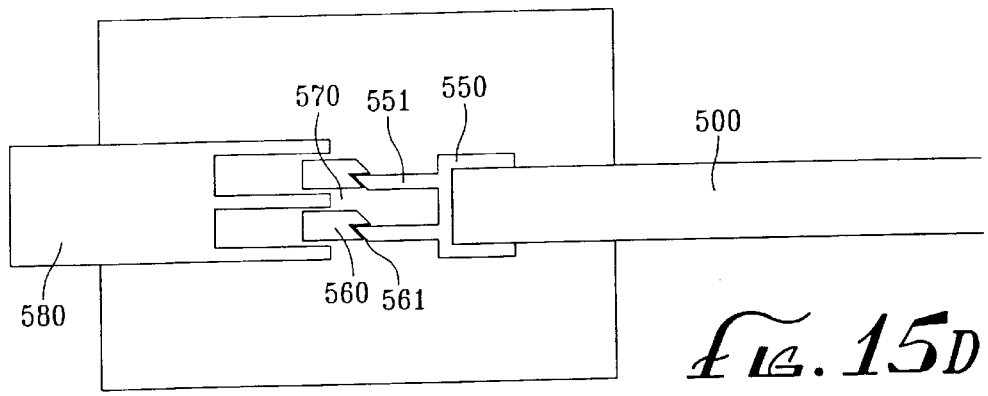
FIG. 15D depicts the proximal end of the obturator of FIG. 15A when the blade is extended distal to the obturator.
Figure 15E:
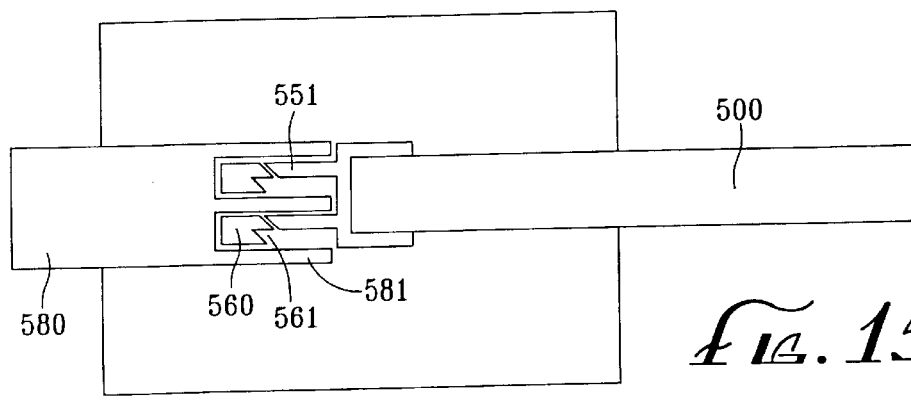
FIG. 15E depicts the proximal end of the obturator of FIG. 15D when a force is applied to a release element.

FIGS. 15B, 15C, 15D, and 15E depict an embodiment of the proximal end of the actuating mechanism when the obturator of FIG. 15A is used to incise a body tissue. Rotary element 550 engages elongate member 500 of the actuating mechanism. The rotary element includes sliding members 551 which extend proximally and engage prongs of release element 580, e.g., a button. When the blade is retracted within the obturator, sliding members of the rotary element engage prongs of release element 580 in slots 570 between two retaining elements 560 as depicted in FIG. 5B. To advance the blade distally, force is applied to release element 580 against the spring at the distal region of the actuating mechanism, causing rotary member 550 and elongate member 500 to slide distally as depicted in FIG. 15C. The blade can be retained distal to the obturator by having sliding members 551 engage slots 561 of retaining elements 560 as depicted in FIG. 15D. After an incision is created on body tissue, the blade is retracted by applying a force to releasing element 580 against the biasing element, causing rotary member 550 and elongate member 500 to slide distally as depicted in FIG. 15E. Sliding members 551 lift out of slots 561 and fall into slots 570 as depicted in FIG. 15B. The above sequence can be repeated for subsequent actuation and de-actuation of the blade. The actuating mechanism described herein is similar to the workings of a ballpoint pen.

Figure 16A:
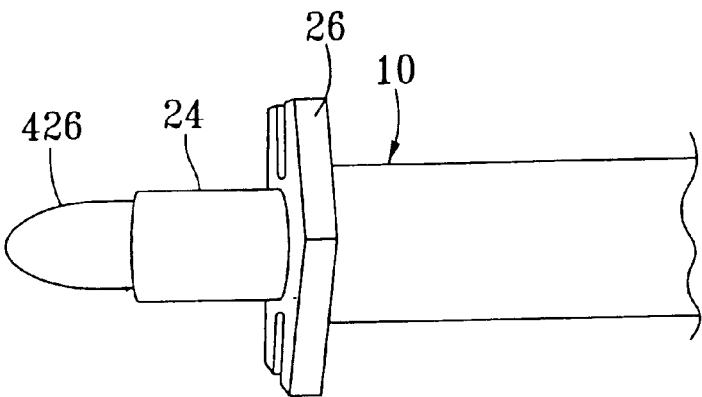
FIG. 16A depicts a lateral view of the obturator/introducer assembly of FIG. 15A having the blade retracted within the obturator.
Figure 16B:
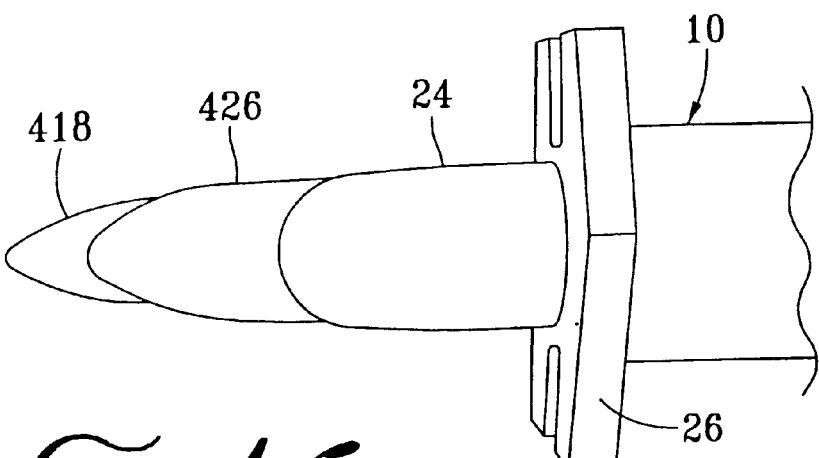
FIG. 16B depicts a lateral view of the obturator/introducer assembly of FIG. 15A having the blade advanced distal to the obturator.

The distal end of the obturator/introducer assembly of FIG. 14C is depicted in FIGS. 16A and 16B. In FIG. 16A, casing 426, which houses cutting element 418, extends distally from distal end 24 of introducer 10. Upon activation, cutting element 418 extends distally from casing 426 as depicted in FIG. 16B.

After the obturator is removed from the obturator/introducer assembly of FIG. 14C, a medical device, such as balloon occlusion device 700, can be inserted into device connector 60 as depicted in FIG. 17. Occlusion device 700 includes proximal end 710 and distal end 704. Expandable balloon 711 is mounted on distal end 704 and communicates with inflation lumen 712. The balloon is placed in a collapsed state to facilitate insertion of occlusion device 700 through device connector 60 and subsequently into introducer 20 and a body cavity, e.g., a blood vessel such as the aorta. Balloon 711 can be inflated by infusing gas, air, or saline through proximal end 710 and lumen 712.

Figure 18:
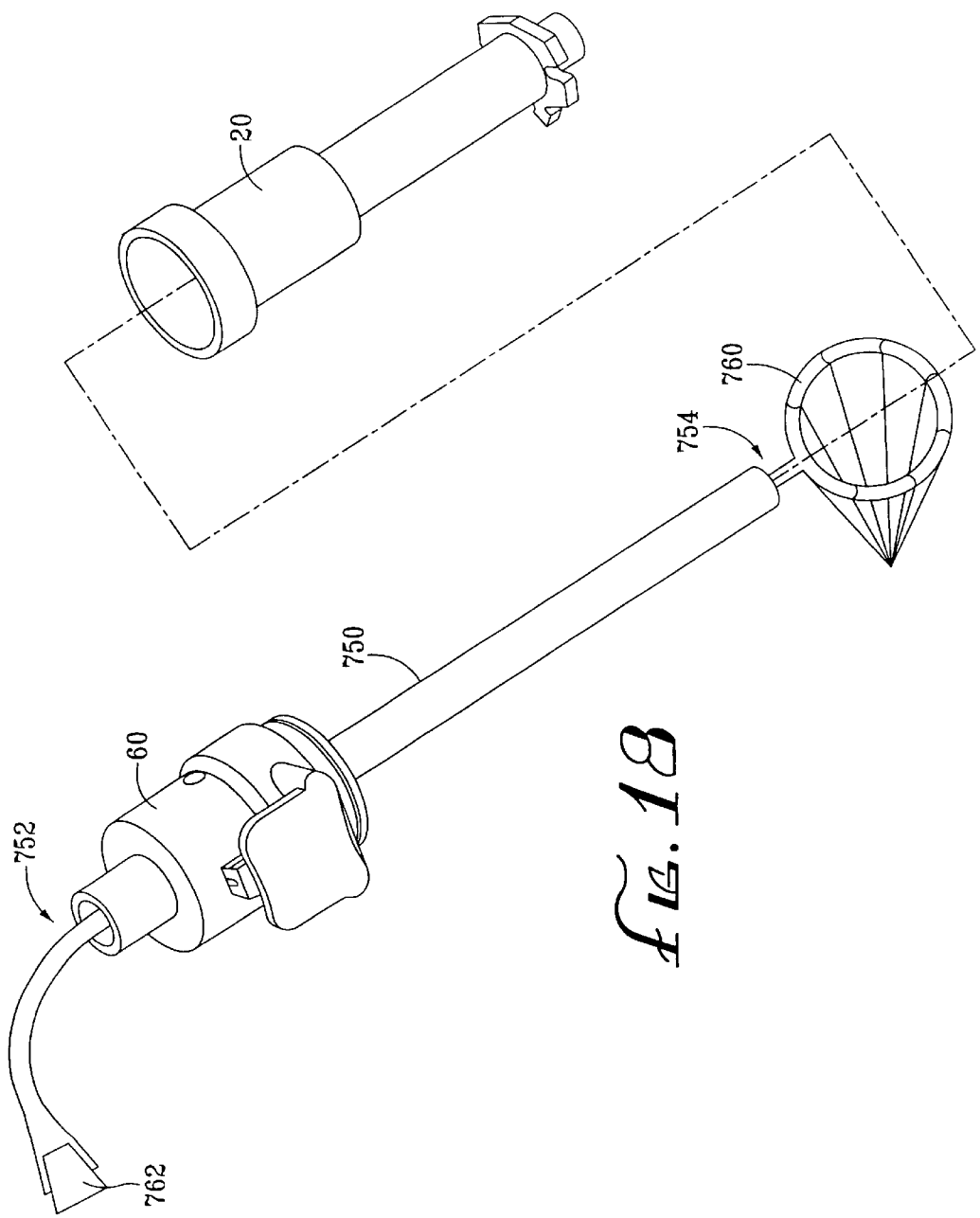
FIG. 18 depicts a filter inserted through the introducer of FIG. 3.

Vascular occlusion can also be achieved by using umbrella or membrane occlusion device 750 as shown in FIG. 18. Occlusion device 750 includes proximal end 752 having an actuation mechanism 762, and distal end 754. Occlusion element 760 is attached to the distal end 754 and is placed in a collapsed state during its insertion into device connector 60 and the introducer. After the occlusion device is inserted into the vessel, vascular occlusion is achieved by expanding occlusion element 760 by operating actuator 762.

FIG. 19 depicts atherectomy device 600 inserted through device connector 60. The atherectomy device includes proximal end 602 having an actuation mechanism 614, and distal end 604. Atherectomy element 610 is attached to distal end 604 and is manipulated via actuation mechanism 614. In use, after atherectomy device 600 is inserted into device connector 60, the assembled unit is inserted through tubular member 20 of the introducer for subsequent introduction into a blood vessel. Aspiration lumen 612 is included in atherectomy device 600 for aspirating calcium, plague, gaseous bubbles, and/or tissue debris generated during atherectomy.

Figure 20A:
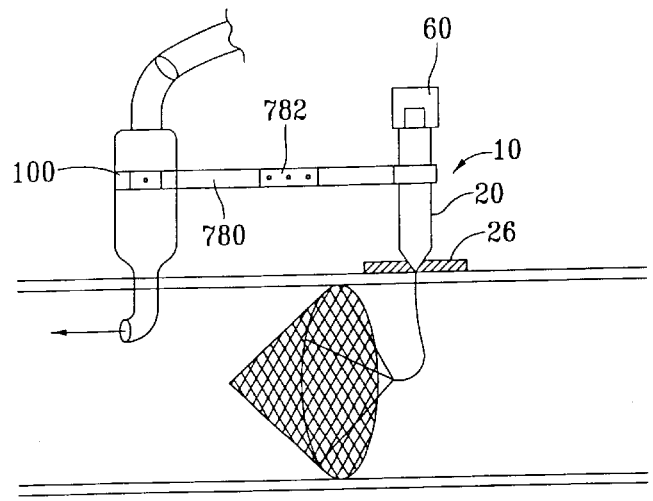
FIG. 20A depicts the introducer of FIG. 18 coupled to a cannula.
Figure 20B:
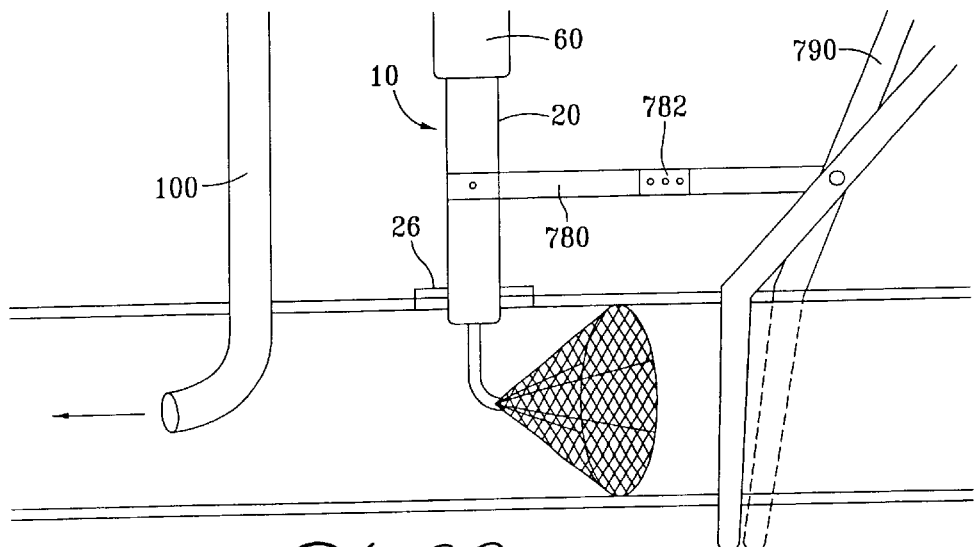
FIG. 20B depicts the introducer of FIG. 18 coupled to an aortic clamp.

In addition to placing sutures on support flange 26, other support mechanisms for securing introducer 10 onto a blood vessel are depicted in FIGS. 20A and 20B. In FIG. 20A, introducer 10 is attached to cannula 100 by a clamp or brace 780. Snaps or tie-on straps 782 are used to secure clamp 780 to cannula 100 and introducer 10 during a surgical procedure. Clamp 780 is preferably rigid and of an adjustable length, thereby allowing variable displacement between the introducer and the cannula. Clamp 780 and straps 782 can also be used to temporarily attach introducer 10 to aortic clamp 790 as shown in FIG. 20B.

Figure 21:
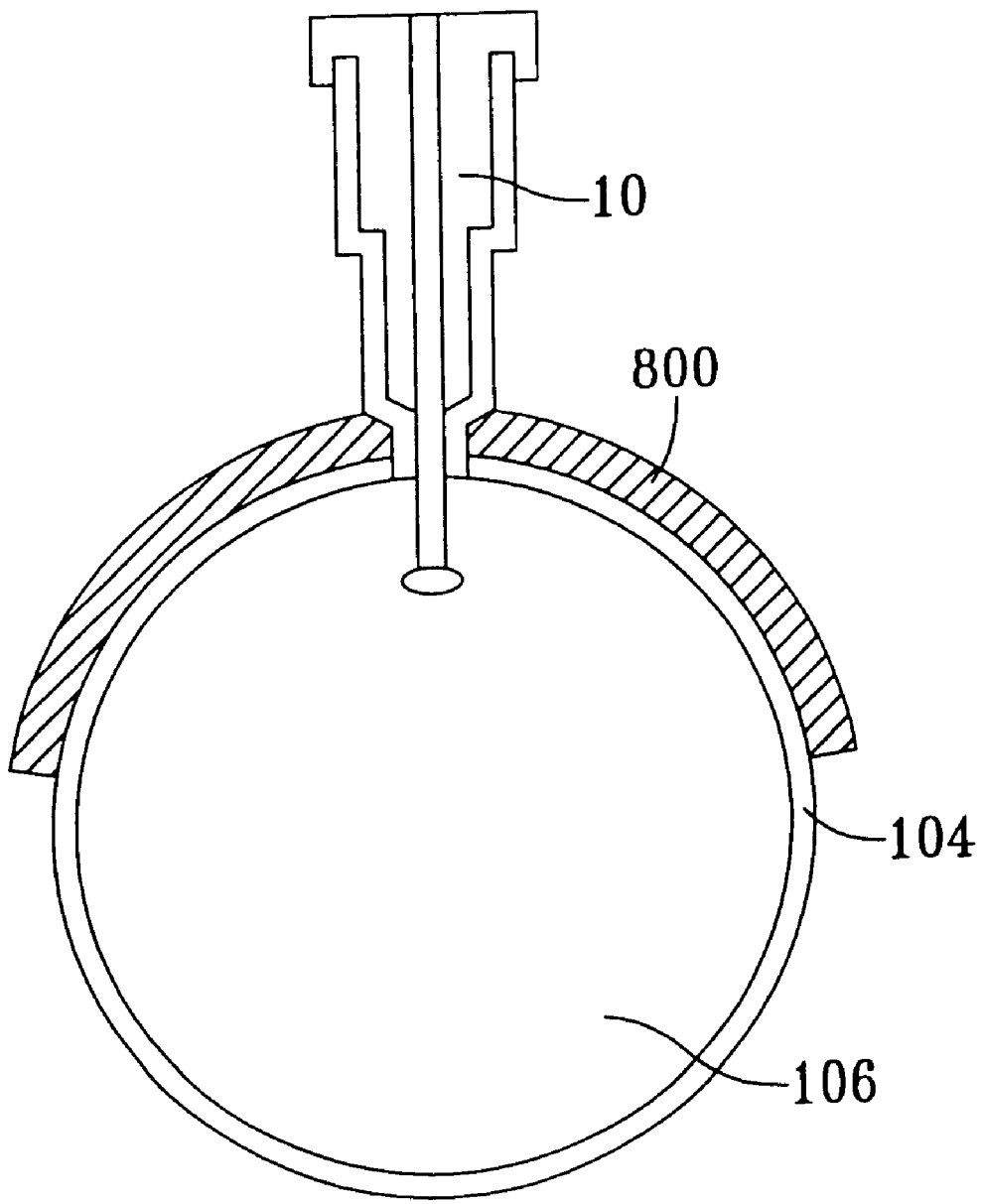
FIG. 21 depicts a cross-sectional view of an introducer having an enlarged flange.

Another supporting mechanism which comprises enlarged support flange 800 is depicted in FIG. 21. The flange is shaped to conform to the contours of the blood vessel. Using an enlarged support flange for device stabilization is particularly useful in performing procedures on large vessels, such as the aorta.

FIG. 22A depicts another embodiment of the introducer having the capability of simultaneously introducing multiple medical devices through a single incision on a body tissue. Second introducer 810 comprises elongate tubular member 820. Device connector 60 is attached to first introducer 10 at distal region 850. A medical device can be inserted into the second introducer through proximal end 866. Alignment pin 864 provides proper attachment between device connector 860 and tubular member 820. Device connector 860 can be detached from the tubular member by depressing release lever 863. In this way, medical devices can be deployed independently through distal end 24 of introducer 10 and distal end 824 of introducer 810 through a single incision. Alternatively, the distal end of second introducer 810 communicates with distal end 24 of introducer 10 as depicted in FIG. 22B.

The length of the introducer will generally be between 4 and 15 centimeters, more preferably approximately 5 to 10 centimeters. The inner diameter of the introducer will generally be between 0.4 and 1.8 centimeters, preferably approximately 0.8 and 1.2 centimeters. The length of the obturator will generally be between 5 and 20 centimeters, preferably approximately 10 and 15 centimeters. The diameter of the obturator will generally be between 0.4 and 1.8 centimeters, preferably approximately 0.8 and 1.2 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for purposes of clarity of understanding, been described in some detail by way of illustration and example, it will be obvious that certain changes and modifications may be practiced which will still fall within the scope of the appended claim. It will also be understood that each feature of each embodiment discussed herein and of each reference cited herein, can be used in combination with the features of any other embodiment.

What is claimed is:

1. A method for creating an incision during cardiovascular surgery on a patient, comprising the steps of:

providing an introducer and an elongate tubular member adapted to fit within a lumen of the introducer, the elongate tubular member having a proximal end and a distal end, a blade mounted within a slot at the distal end of the elongate tubular member, an actuating mechanism having a distal end connected to a proximal end of the blade, and a proximal end operable from the proximal end of the elongate tubular member, wherein the actuating mechanism slides proximal when released and the blade retracts to a position within the slot, and wherein the actuating mechanism is operated to slide distally, and is retained in a distal position and the blade extends distally beyond the slot and the distal end of the elongate tubular member;

activating the blade by advancing the actuating mechanism;

making an incision in an aorta using the blade and without cutting the patient's heart;

inserting the introducer through the incision;

operating the actuating mechanism to release the blade into the slot;

removing the elongate tubular member from the introducer; and advancing a medical device through the lumen of the introducer and into the aorta.

2. The method of claim 1, further comprising the step of performing surgery on the beating heart.

3. The method of claim 1, wherein the actuating mechanism further comprises a force biasing element, and wherein the force biasing element is a spring.

4. The method of claim 1, wherein the actuating mechanism is an elongate member.

5. The method of claim 1, wherein the actuating mechanism further comprises a finger actuated button which is depressed to advance the actuating mechanism distally into engagement with a retaining element, and when actuated again, advances the actuating mechanism beyond the retaining element and into a release, wherein the actuating mechanism slides proximally.

6. An introducer, comprising:

an elongate tubular member having a proximal end, a distal end, and a lumen therebetween, the distal end adapted to enter a vessel, the proximal end having a longitudinal slot extending distally from the proximal end; and a device connector having a first end, a second end, and a lumen therebetween, the lumen adapted to receive a medical device and thereafter release said device, the device connector further comprising an alignment mechanism and being shaped to engage the proximal end of the elongate tubular member by operation of a release lever, wherein the elongate tubular member is linked to a cross-clamp.

7. An introducer, comprising:

an elongate tubular member having a proximal end, a distal end, and a lumen therebetween, the distal end adapted to enter a vessel, the proximal end having a longitudinal slot extending distally from the proximal end;

a device connector having a first end, a second end, and a lumen therebetween, the lumen adapted to receive a medical device and thereafter release said device, the device connector further comprising an alignment mechanism and being shaped to engage the proximal end of the elongate tubular member by operation of a release lever; and a second elongate tubular member having a proximal end, a distal end, and a lumen therebetween, the distal end adapted to enter a vessel, the proximal end having a longitudinal slot extending distally from the proximal end; and a second device connector having a first end, a second end, and a lumen therebetween, the lumen adapted to receive a medical device and thereafter release said device, the device connector further comprising an alignment pin adapted to engage the alignment slot of the elongate tubular member, and being shaped to engage the proximal end of the elongate tubular member by operation of a release lever.

* * * * *